United States Patent
Horiuchi et al.

(10) Patent No.: US 8,293,383 B2
(45) Date of Patent: Oct. 23, 2012

(54) BENZO[A]FLUORANTHENE COMPOUND AND ORGANIC LIGHT EMITTING DEVICE USING THE SAME

(75) Inventors: Takayuki Horiuchi, Tokyo (JP); Naoki Yamada, Inagi (JP); Satoshi Igawa, Fujisawa (JP); Masashi Hashimoto, Tokyo (JP); Minako Nakasu, Tokyo (JP); Jun Kamatani, Tokyo (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 523 days.

(21) Appl. No.: 12/438,640

(22) PCT Filed: May 15, 2008

(86) PCT No.: PCT/JP2008/059392
§ 371 (c)(1),
(2), (4) Date: Feb. 24, 2009

(87) PCT Pub. No.: WO2008/140133
PCT Pub. Date: Nov. 20, 2008

(65) Prior Publication Data
US 2010/0237328 A1    Sep. 23, 2010

(30) Foreign Application Priority Data

May 16, 2007   (JP) .................. 2007-130526
Apr. 2, 2008   (JP) .................. 2008-095675

(51) Int. Cl.
H01L 51/54    (2006.01)
C09K 11/06    (2006.01)

(52) U.S. Cl. .......... 428/690; 428/917; 313/504; 257/40; 585/27; 564/308

(58) Field of Classification Search ........................ None
See application file for complete search history.

(56) References Cited

U.S. PATENT DOCUMENTS

| | | | |
|---|---|---|---|
| 3,029,236 A | 4/1962 | Staeuble et al. | |
| 2003/0027016 A1 | 2/2003 | Ara et al. | 428/690 |
| 2004/0031957 A1* | 2/2004 | Tyan | 257/40 |
| 2004/0076853 A1 | 4/2004 | Jarikov | 428/690 |
| 2004/0131881 A1 | 7/2004 | Zheng et al. | |
| 2004/0147742 A1* | 7/2004 | Wong et al. | 544/230 |
| 2004/0253389 A1* | 12/2004 | Suzuki et al. | 428/1.1 |
| 2007/0249878 A1 | 10/2007 | Iwawaki et al. | 585/27 |
| 2007/0252141 A1 | 11/2007 | Negishi et al. | 257/40 |
| 2008/0272692 A1 | 11/2008 | Hashimoto et al. | 313/504 |
| 2008/0286611 A1 | 11/2008 | Muratsubaki et al. | 428/704 |
| 2009/0033210 A1 | 2/2009 | Saitoh et al. | 313/504 |
| 2009/0066227 A1 | 3/2009 | Okinaka et al. | 313/504 |
| 2009/0079344 A1 | 3/2009 | Saitoh et al. | 313/504 |
| 2009/0102371 A1 | 4/2009 | Hashimoto et al. | 313/504 |
| 2009/0134788 A1 | 5/2009 | Yamada et al. | 313/504 |

FOREIGN PATENT DOCUMENTS

| | | |
|---|---|---|
| EP | 1757670 A2 | 2/2007 |
| JP | 10-189247 | 7/1998 |
| JP | 10340785 A | 12/1998 |
| JP | 2002-008867 | 1/2002 |
| JP | 2003-347058 | 12/2003 |
| JP | 2004002351 A | 1/2004 |
| JP | 2007027356 A | 2/2007 |

OTHER PUBLICATIONS

Hughes et al. "Electron-transporting materials for organic electroluminescent and electrophosphorescent devices" J. Mater. Chem. 2005, 15, 94-107.*
U.S. Appl. No. 12/295,240, filed Mar. 13, 2007.
U.S. Appl. No. 12/296,574, filed Oct. 9, 2008.
International Preliminary Report on Patentability issued Nov. 26, 2009 in PCT/JP2008/059392, 5 pages.
Murov et al., "Photophysics of Organic Molecules in Solution," *Handbook of Photochemistry*, vol. 1, Sec. 1, pp. 1-3, 8-11, 14, 15, 20, 21, 26, 27, 36, & 37 (1993).
Nijegorodov et al., "The Influence of Planarity and Rigidity on the Absorption and Fluorescence Parameters and Intersystem Crossing Rate Constant in Aromatic Molecules," *J. Phys. Chem.*, vol. 98, No. 22, 5639-5643 (1994).
Huang et al., "Benzo[a]aceanthrylene Derivatives for Red-Emitting Electroluminescent Materials," *Chem. Mater.*, vol. 15, 4854-4862 (2003).
U.S. Appl. No. 12/438,894, filed May 15, 2008.
U.S. Appl. No. 12/438,629, filed May 15, 2008.

* cited by examiner

*Primary Examiner* — Lynda Salvatore
*Assistant Examiner* — Andrew K Bohaty
(74) *Attorney, Agent, or Firm* — Fitzpatrick, Cella, Harper & Scinto

(57) ABSTRACT

There is provided a benzo[a]fluoranthene compound represented by the formula (I):

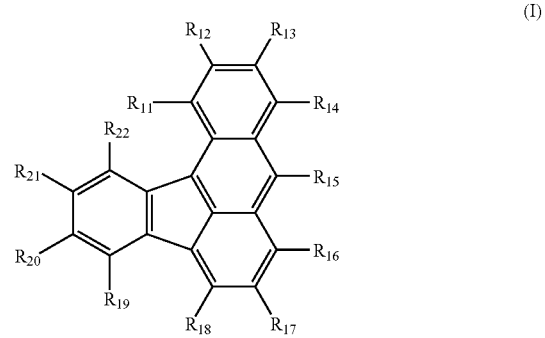

wherein: at least one $R_{11}$ to $R_{22}$ represents $R_m$ represented by the formula (i):

$$R_m = -Ar_1 - X_1 \qquad (i)$$

wherein: $Ar_1$ represents any one of the following groups (i-a) to (i-c): (i-a) a substituted or unsubstituted phenylene group, (i-b) a substituted or unsubstituted monocyclic heterocyclic group, and (i-c) a composite substituent formed of two substituents selected from substituents corresponding to the groups (i-a) and (i-b); and $X_1$ represents a substituted or unsubstituted alkyl group having 2 or more carbon atoms, a substituted or unsubstituted alkenyl group, or a substituted or unsubstituted alkynyl group; and $R_{11}$ to $R_{22}$ none of which is represented by $R_m$ each represent a hydrogen atom, a halogen atom or the like, and $R_{11}$ to $R_{22}$ none of which is represented by $R_m$ may be identical to or different from each other.

8 Claims, 3 Drawing Sheets

BENZO[A]FLUORANTHENE COMPOUND AND ORGANIC LIGHT EMITTING DEVICE USING THE SAME

TECHNICAL FIELD

The present invention relates to a benzo[a]fluoranthene compound and an organic light emitting device using the compound.

BACKGROUND ART

An organic light emitting device is a device in which a thin film including a fluorescent organic compound or a phosphorescent organic compound is sandwiched between an anode and a cathode. Further, electrons and holes are injected from the respective electrodes to generate exciton of the fluorescent compound or the phosphorescent compound, whereby the organic light emitting device emits light when the exciton return to a ground.

Recent progress of an organic light emitting device is remarkable, and the characteristics of the device enable a light emitting device with a high luminance at a low applied voltage, a variety of emission wavelengths, high-speed responsiveness, thin and light weight. From this fact, it is suggested that the device have potential to find use in a wide variety of applications.

However, the present situation calls for optical output with even higher luminance or higher conversion efficiency. In addition, many problems still remain to be solved regarding durability against the change over time due to long-term use, deterioration caused by atmospheric gas containing oxygen, moisture, or the like.

Further, when considering application to a full color display or similar device, the present art is still insufficient against problems relating to the needs for light emission of blue, green, and red with a high color purity.

The use of a benzofluoranthene compound as a component for an organic light emitting device has been proposed as a method of solving the above-mentioned problems. For example, in each of Japanese Patent Application Laid-Open No. 10-189247, Japanese Patent Application Laid-Open No. 2002-8867, and Chem. Master. 2003, 15, 4854-4862, a benzofluoranthene compound is used as a component for an organic light emitting device.

DISCLOSURE OF THE INVENTION

An object of the present invention is to provide a novel benzo[a]fluoranthene compound. Another object of the present invention is to provide an organic light emitting device having extremely good light emitting efficiency, extremely good luminance, and durability.

A benzo[a]fluoranthene compound of the present invention is represented by the following general formula (I).

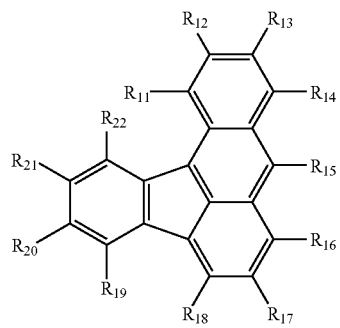

(I)

wherein:
at least one of $R_{11}$ to $R_{22}$ represents $R_m$ represented by the following general formula (i):

(i)

wherein:
$Ar_1$ represents any one of the following groups (i-a) to (i-c):
(i-a) a substituted or unsubstituted phenylene group,
(i-b) a substituted or unsubstituted, monocyclic heterocyclic group, and
(i-c) a composite substituent formed of two substituents selected from substituents corresponding to the groups (i-a) and (i-b); and $X_1$ represents a substituted or unsubstituted alkyl group having 2 or more carbon atoms, a substituted or unsubstituted alkenyl group, or a substituted or unsubstituted alkynyl group; and $R_{11}$ to $R_{22}$ none of which is represented by $R_m$ each represent a hydrogen atom, a halogen atom, a cyano group, a nitro group, a substituted or unsubstituted alkyl group, a substituted or unsubstituted alkoxy group, a substituted or unsubstituted alkenyl group, a substituted or unsubstituted alkynyl group, a substituted or unsubstituted aralkyl group, or a substituted or unsubstituted amino group, and $R_{11}$ to $R_{22}$ none of which is represented by $R_m$ may be identical to or different from each other.

According to the present invention, there can be provided a novel benzo[a]fluoranthene compound. In addition, according to the present invention, there can be provided an organic light emitting device having extremely good light emitting efficiency, extremely good luminance, and durability.

BEST MODE FOR CARRYING OUT THE INVENTION

Figure 1:
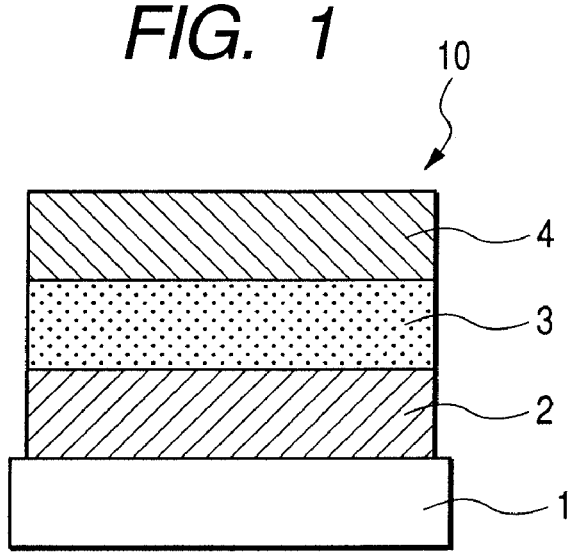
FIG. 1 is a cross sectional view illustrating an organic light emitting device according to a first embodiment of the present invention.

First, a benzo[a]fluoranthene compound of the present invention will be described.

Here, the first embodiment of the benzo[a]fluoranthene compound of the present invention is a compound represented by the following general formula (I).

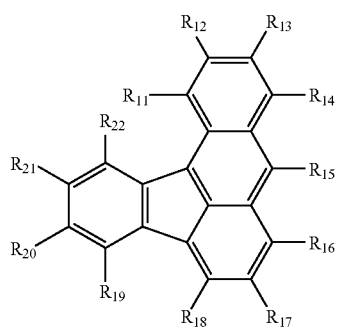
(I)

In the general formula (I), at least one of $R_{11}$ to $R_{22}$ represents $R_m$ represented by the following general formula (i):

(i)

wherein:
$Ar_1$ represents any one of the following groups (i-a) to (i-c):
(i-a) a substituted or unsubstituted phenylene group,
(i-b) a substituted or unsubstituted monocyclic heterocyclic group, and
(i-c) a composite substituent formed of two substituents selected from substituents corresponding to the groups (i-a) and (i-b).

Examples of the monocyclic heterocyclic group (i-b) represented by $Ar_1$ include thiophene, pyrrole, pyridine, pyrazine, pyrimidine, oxazole, oxadiazole, thiazole, and thiadiazole.

Examples of the composite substituent (i-c) represented by $Ar_1$ include a biphenyl group, a phenylpyridyl group, a phenyloxazole group, a bipyridyl group, a phenylpyrimidyl group, and a phenylpyridyl group.

Examples of the substituent that the substituents represented by the groups (i-a) to (i-c) may have include: alkyl groups such as a methyl group, an ethyl group, and a propyl group; aralkyl groups such as a benzyl group and a phenethyl group; amino groups such as a dimethylamino group, a diethylamino group, a dibenzylamino group, a diphenylamino group, a ditolylamino group, and a dianisolylamino group; alkoxy groups such as a methoxy group, an ethoxy group, a propoxy group, and a phenoxy group; a cyano group; a nitro group; and halogen atoms such as fluorine and chlorine.

In the general formula (i), $X_1$ represents a substituted or unsubstituted alkyl group having 2 or more carbon atoms, a substituted or unsubstituted alkenyl group, or a substituted or unsubstituted alkynyl group.

Examples of the alkyl group represented by $X_1$ include an ethyl group, an isopropyl group, a t-butyl group, and an adamanthyl group. Preferable alkyl group is a t-butyl group or an adamanthyl group.

Examples of the alkenyl group represented by $X_1$ include a vinyl group and a butenyl group.

Examples of the alkynyl group represented by $X_1$ include an ethynyl group and a butynyl group.

Examples of the substituent that the alkyl group, the alkenyl group, and the alkynyl group may have include: alkyl groups such as a methyl group, an ethyl group, a propyl group, and a t-butyl group; aralkyl groups such as a benzyl group and a phenethyl group; aryl groups such as a phenyl group, a biphenyl group, a 2,4,6-trimethylphenyl group, a 4-t-butylphenyl group, and a 3,5-di-t-butylphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; alkoxy groups such as a methoxy group, an ethoxy group, a propoxy group, and a phenoxy group; a cyano group; a nitro group; and halogen atoms such as fluorine and chlorine.

Further, in general formula (I), $R_{11}$ to $R_{22}$ none of which is represented by $R_m$ each represent a hydrogen atom, a halogen atom, a cyano group, a nitro group, a substituted or unsubstituted alkyl group, a substituted or unsubstituted alkoxy group, a substituted or unsubstituted aryloxy group, a substituted or unsubstituted alkenyl group, a substituted or unsubstituted alkynyl group, a substituted or unsubstituted aralkyl group, or a substituted or unsubstituted amino group.

Examples of the halogen atom represented by $R_{11}$ to $R_{22}$ include fluorine, chlorine, bromine, and iodine.

Examples of the alkyl group represented by $R_{11}$ to $R_{22}$ include a methyl group, an ethyl group, a normal propyl group, an isopropyl group, a normal butyl group, a t-butyl group, a sec-butyl group, an octyl group, a 1-adamanthyl group, and a 2-adamanthyl group.

Examples of the alkoxy group represented by $R_{11}$ to $R_{22}$ include a methoxy group, an ethoxy group, and a propoxy group.

Examples of the aryloxy group represented by $R_{11}$ to $R_{22}$ include a phenoxy group, a 4-methylphenoxy group, and a naphthoxy group.

Examples of the alkenyl group represented by $R_{11}$ to $R_{22}$ include a vinyl group, a propenyl group, a butenyl group, a phenylvinyl group, and a diphenylvinyl group.

Examples of the alkynyl group represented by $R_{11}$ to $R_{22}$ include an ethynyl group, a propinyl group, a butinyl group, and a phenethynyl group.

Examples of the aralkyl group represented by $R_{11}$ to $R_{22}$ include a benzyl group and a phenethyl group.

Examples of the amino group represented by $R_{11}$ to $R_{22}$ include a dimethylamino group, a diethylamino group, a dibenzylamino group, a diphenylamino group, a ditolylamino group, a di-t-butylamino group, a dianisolylamino group, and a carbazoyl group.

Examples of the substituent that the alkyl group may have include: alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, and a dianisolylamino group; alkoxy groups such as a methoxy group, an ethoxy group, and a propoxy group; aryloxy groups such as an alkoxy group and a phenoxy group; halogen atoms such as fluorine and chlorine; a cyano group; and a nitro group.

$R_{11}$ to $R_{22}$ none of which is represented by $R_m$ may be identical to or different from each other.

Since an unsubstituted benzo[a]fluoranthene is of a structure having high planarity, the benzo[a]fluoranthene is apt to cause a reduction in luminance of an organic light emitting device due to concentration quenching in a light emitting layer. In view of the foregoing, when at least one of $R_{11}$ to $R_{22}$ in the general formula (I) represents $R_m$ having large steric hindrance, the concentration quenching in the light emitting layer is suppressed, so the reduction in luminance of the organic light emitting device can be suppressed.

In addition, the introduction of $X_1$ formed of a carbon chain enables the π-conjugate planes of the molecules of the benzo[a]fluoranthene compound to avoid overlapping each other. As a result, the sublimation property and deposition stability of the benzo[a]fluoranthene compound are improved, the crystallinity of the compound is reduced, and the stability of a film formed of the compound is improved by the high glass transition temperature of the compound.

Hereinafter, specific examples of the compound represented by the general formula (I) will be shown below. However, the present invention is not limited to these examples.

A-1

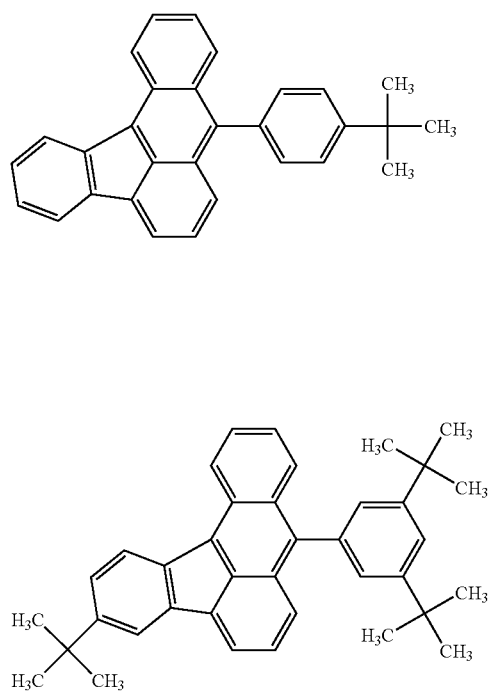

A-2

A-3

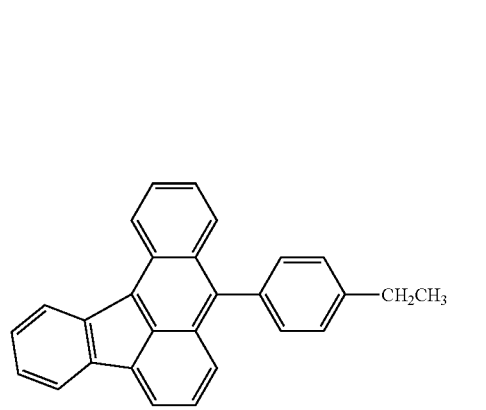

-continued

A-4

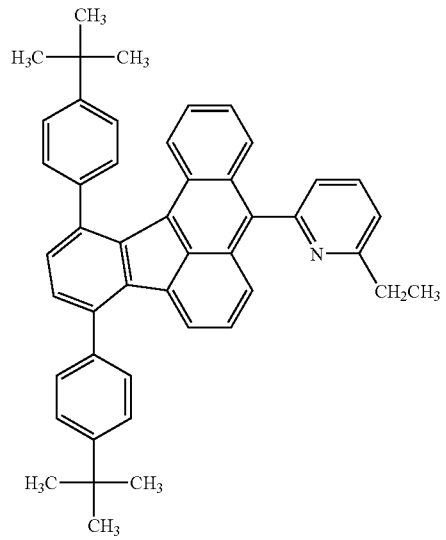

A-5

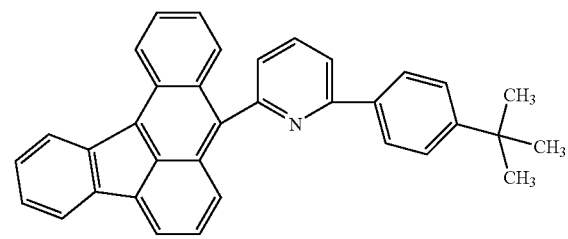

A-6

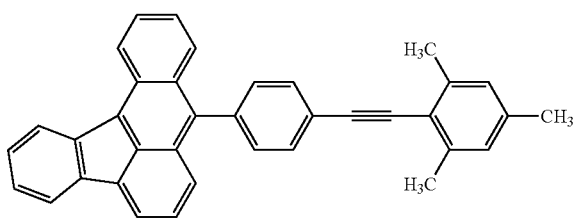

A-7

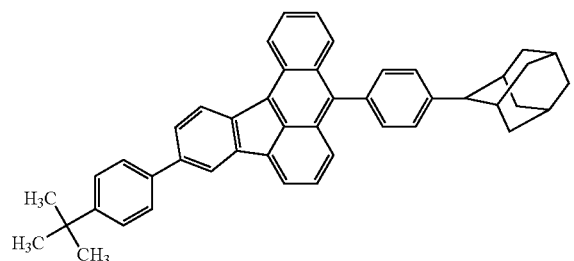

A-8

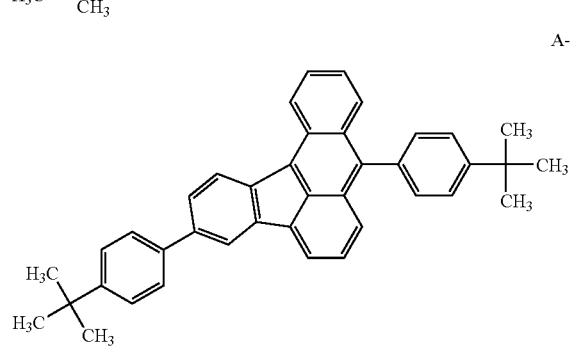

-continued

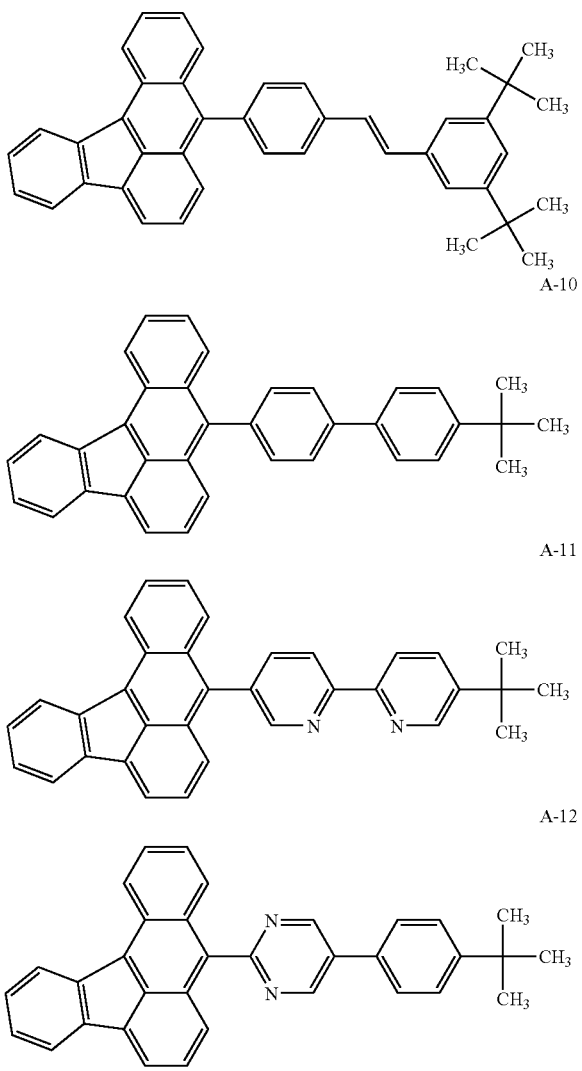

The benzo[a]fluoranthene compound of the present invention can be used as a material of which an organic light emitting device is formed. In addition, the incorporation of the benzo[a]fluoranthene compound of the present invention as a component for the organic light emitting device improves the light emitting efficiency, color purity, and durability of the organic light emitting device. The reason why those properties are improved will be described below.

The benzo[a]fluoranthene compound of the present invention contains a five-membered ring structure. Here, the benzo[a]fluoranthene compound of the present invention is provided with electron injecting property by virtue of electron withdrawing property resulting from the five-membered ring structure. Accordingly, the use of the benzo[a]fluoranthene compound of the present invention as a material of which the organic light emitting device is formed can reduce the voltage at which the device is driven because the use allows an electron generated from a cathode to be efficiently transported. As a result, the light emitting efficiency of the organic light emitting device can be improved. In addition, the use contributes also to the lengthening of the lifetime of the organic light emitting device.

In addition, the introduction of a substituent into the benzo[a]fluoranthene compound of the present invention can appropriately adjust the levels of the HOMO and LUMO of the compound. Accordingly, a molecule of the compound can be designed while a balance between the amount in which a hole as a carrier is injected and the amount in which an electron as another carrier is injected is taken into consideration.

The chemical stability of a material of which an organic light emitting device is formed is an important factor for the durability of the device.

The benzo[a]fluoranthene compound of the present invention is chemically stable because the compound shows low reactivity against the electrophilic reaction of a singlet oxygen molecule or the like by virtue of an electron withdrawing effect originating from the five-membered ring structure.

In addition, the chemical stability of the benzo[a]fluoranthene compound of the present invention is additionally improved when the compound has a substituent in its benzo[a]fluoranthene skeleton. The substituent is preferably a substituent formed of a carbon atom and a hydrogen atom. To be specific, an alkyl group, an alkenyl group, an alkynyl group, an aralkyl group, or an aryl group is preferable, and an alkyl group or an aryl group is more preferable.

In contrast, a nitrogen atom-containing substituent such as an amino group is not preferable because the substituent is a substituent having high chemical reactivity, and reduces the chemical stability of the benzo[a]fluoranthene compound.

Here, the substituent formed of a carbon atom and a hydrogen atom is preferably introduced into the position of $R_{15}$ in the benzo[a]fluoranthene compound of the formula (I). Since the position is the substitution position at which electrophilic reactivity is highest in the benzo[a]fluoranthene skeleton, the introduction of a substituent having a lower elimination ability and lower chemical reactivity than those of a hydrogen atom into the position additionally improves the chemical stability of the benzo[a]fluoranthene compound. In addition, an alkoxy group or a heterocyclic group as well as a substituent formed of a carbon atom and a hydrogen atom (such as an alkyl group, an alkenyl group, an alkynyl group, an aralkyl group, or an aryl group) may be introduced into the position.

Next, an organic light emitting device of the present invention will be described in detail.

The organic light emitting device of the present invention includes an anode, a cathode, and a layer formed of an organic compound, the layer being interposed between the anode and cathode. In addition, the layer formed of an organic layer contains at least one kind of a benzo[a]fluoranthene compound of the present invention.

Hereinafter, an organic light emitting device of the present invention will be described in detail with reference to the drawings.

Reference numeral 1 denotes a substrate; 2, an anode; 3, a light emitting layer; 4, a cathode; 5, a hole transporting layer; 6, an electron transporting layer; 7, a hole injecting layer; 8, a hole/exciton blocking layer; and 10, 20, 30, 40, and 50 each denote an organic light emitting device.

FIG. 1 is a cross sectional view illustrating an organic light emitting device according to a first embodiment of the present invention. The organic light emitting device 10 of FIG. 1 includes the anode 2, the organic light emitting layer 3, and the cathode 4, which are sequentially formed on the substrate 1. The organic light emitting device 10 is useful in a case where the light emitting layer 3 is formed of a compound which has all the properties including a hole transporting ability, an electron transporting ability, and light emitting property or a case where the light emitting layer 3 is formed of a mixture of compounds each having one of the hole transporting ability, the electron transporting ability, and the light emitting property.

Figure 2:
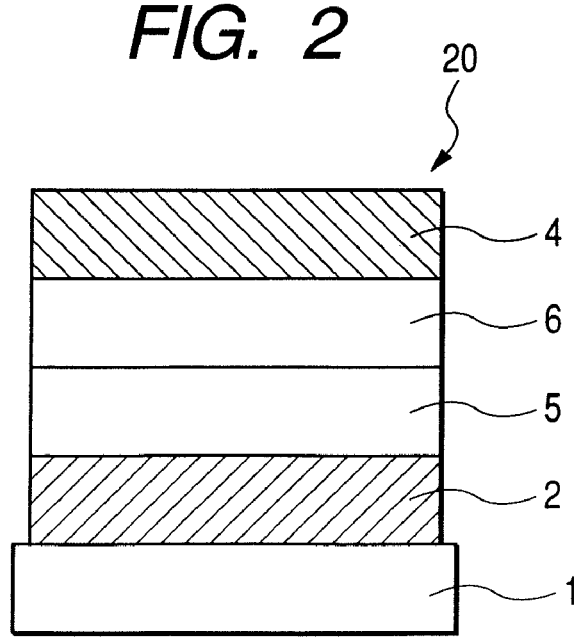
FIG. 2 is a cross sectional view illustrating an organic light emitting device according to a second embodiment of the present invention.

FIG. 2 is a cross sectional view illustrating the organic light emitting device according to a second embodiment of the present invention. The organic light emitting device 20 of FIG. 2 includes the anode 2, the hole transporting layer 5, the electron transporting layer 6, and the cathode 4, which are sequentially formed on the substrate 1. The organic light emitting device 20 is useful in a case where a light emitting organic compound having one of hole transporting property and electron transporting property and an organic compound having electron transporting property alone or hole transporting property alone are used in combination. In addition, in the light emitting device 20, the hole transporting layer 5 or the electron transporting layer 6 serves as the light emitting layer.

Figure 3:
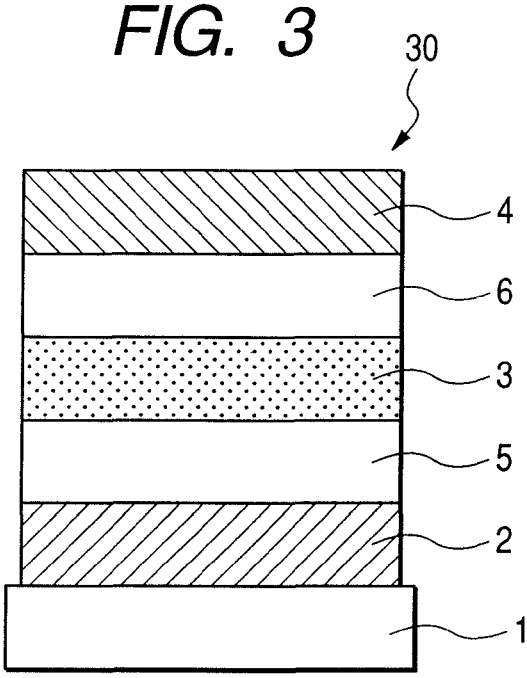
FIG. 3 is a cross sectional view illustrating an organic light emitting device according to a third embodiment of the present invention.

FIG. 3 is a cross sectional view illustrating the organic light emitting device according to a third embodiment of the present invention. The organic light emitting device 30 of FIG. 3 illustrate a structure in which the light emitting layer 3 is inserted between the hole transporting layer 5 and the electron transporting layer 6 in the organic light emitting device 20 of FIG. 2. In the organic light emitting device 30, a carrier transporting function and a light emitting function are separated from each other. Thus, the device can be used appropriately in combination with organic compounds each having one of the hole transporting property, electron transporting property, and light emitting property. Therefore, the degree of freedom in selection of a material extremely increases as well as various compounds different from each other in emission wavelength can be used. As a result, the range of luminescent colors can be widened. Further, a light emitting efficiency of the organic light emitting device 30 can be improved by effectively trapping carrier or exciton in the central light emitting layer 3.

Figure 4:
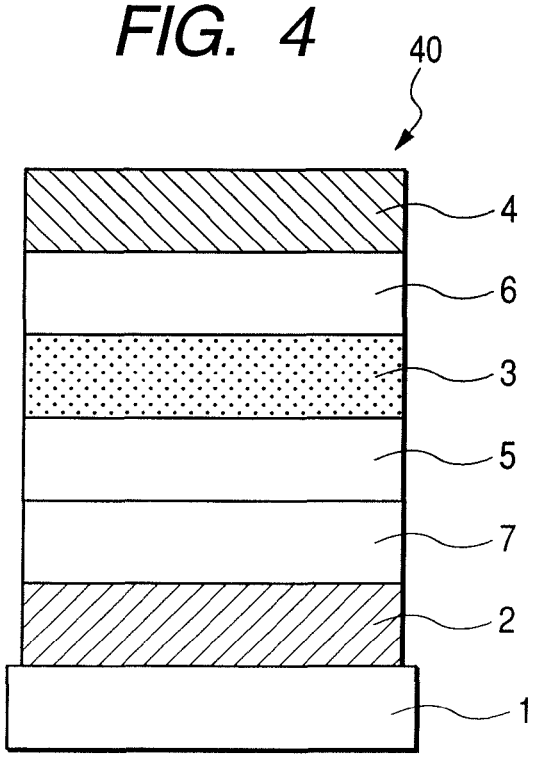
FIG. 4 is a cross sectional view illustrating an organic light emitting device according to a fourth embodiment of the present invention.

FIG. 4 is a cross sectional view illustrating the organic light emitting device according to a fourth embodiment of the present invention. The organic light emitting device 40 of FIG. 4 illustrate a structure in which the hole injecting layer 7 is provided between the anode 2 and the hole transporting layer 5 in the organic light emitting device 30 of FIG. 3. The provision of the hole injecting layer 7 in the organic light emitting device 40 imparts an improving effect on adhesiveness between the anode 2 and the hole transporting layer 5 or on hole injection property, and is effective for a reduction in voltage at which the device is driven.

Figure 5:
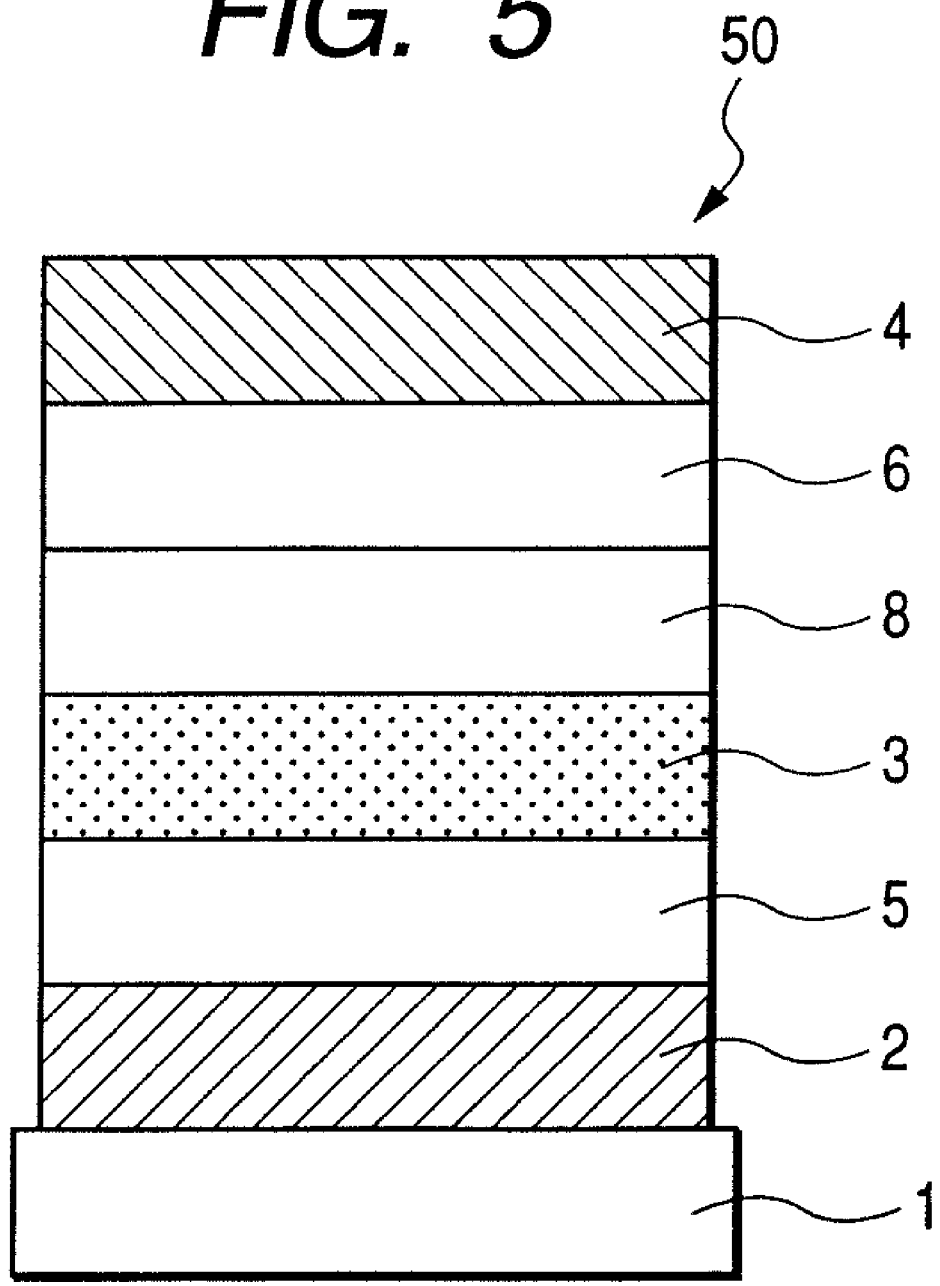
FIG. 5 is a cross sectional view illustrating an organic light emitting device according to a fifth embodiment of the present invention.

FIG. 5 is a cross sectional view illustrating the organic light emitting device according to a fifth embodiment of the present invention. The organic light emitting device 50 of FIG. 5 illustrate a structure in which a layer for inhibiting the escape of a hole or exciton toward the side of the cathode 4 (hole/exciton blocking layer 8) is inserted between the light emitting layer 3 and the electron transporting layer 6 in the organic light emitting device 30 of FIG. 3. The use of a compound having an extremely high ionization potential as the hole/exciton blocking layer 8 improves the light emitting efficiency of the organic light emitting device 50.

It should be noted that the device structures according to the first to fifth embodiments are each merely very basic one, and the structure of the organic light emitting device using the benzo[a]fluoranthene compound of the present invention is not limited to those. For example, an insulating layer may be provided onto an interface between an electrode and an organic layer, an adhesive layer or an interference layer may be provided thereonto, and a hole transporting layer may be formed of two layers having different ionization potentials.

The benzo[a]fluoranthene compound of the present invention can be used in any one of the above-mentioned first to fifth embodiments.

The benzo[a]fluoranthene compound of the present invention can be used as a material for an organic light emitting device. To be specific, the compound can be used as a material of which each of the hole transporting layer, electron transporting layer, and light emitting layer of the device is formed. In this case, one benzo[a]fluoranthene compound of the above kind may be used, or multiple benzo[a]fluoranthene compounds of the above kind may be used. Alternatively, the benzo[a]fluoranthene compound may be incorporated into each of multiple layers. The use of the benzo[a]fluoranthene compound of the present invention improves the light emitting efficiency and lifetime of the organic light emitting device.

The benzo[a]fluoranthene compound of the present invention is particularly preferably used as a material of which the light emitting layer is formed not only because the compound can be used in any one of various embodiments but also because the performance of the organic light emitting device can be improved in terms of color purity, light emitting efficiency, and lifetime.

The light emitting layer may be formed only of the benzo[a]fluoranthene compound of the present invention. Alternatively, the light emitting layer may be formed of a host and a guest. Here, the benzo[a]fluoranthene compound of the present invention can be used in any one of a dopant material serving as a guest, and a fluorescent material and a phosphorescent material each serving as a host. The use of the benzo[a]fluoranthene compound of the present invention as a host or guest in the light emitting layer can improve the performance of the organic light emitting device in terms of color purity, light emitting efficiency, and lifetime.

When the benzo[a]fluoranthene compound of the present invention is used as a guest for the light emitting layer, the corresponding host, which is not particularly limited, is preferably a fused polycyclic derivative from the following viewpoint: an organic light emitting device formed of a stable amorphous film should be provided. Here, in order that an organic light emitting device having high efficiency and durability may be provided, the emission quantum yield of the host itself must be high, and the host itself must be chemically stable. A preferable fused polycyclic derivative satisfying those requests is, for example, a fluorene derivative, a pyrene derivative, a fluoranthene derivative, or a benzofluoranthene derivative. Each of those derivatives has a high emission quantum yield, and is chemically stable.

Here, when the benzo[a]fluoranthene compound of the present invention is used as a guest for the light emitting layer, the content of the compound is preferably 0.1 wt % or more to 30 wt % or less with respect to the total weight of the materials of which the light emitting layer is formed; the content is more preferably 0.1 wt % or more to 15 wt % or less from the viewpoint of the suppression of concentration quenching.

On the other hand, when the benzo[a]fluoranthene compound of the present invention is used as a host for the light emitting layer, the corresponding guest is not particularly limited, and can be appropriately selected depending on, for example, a desired luminescent color. In addition, a hole transportable compound, an electron transportable compound, or the like as well as the guest can be used as required by doping the layer with such compound together with the guest.

The organic light emitting device of the present invention uses the benzo[a]fluoranthene compound of the present invention particularly as a material of which the light emitting layer of the device is formed. In addition, the organic light emitting device of the present invention can use, for example, any one of the conventionally known low-molecular-weight-based and polymer-based hole transportable compounds, luminous compounds, and electron transportable compounds together with the benzo[a]fluoranthene compound of the present invention as required.

Examples of the hole transportable compounds include triarylamine derivatives, aryldiamine derivatives, phthalocyanine derivatives, porphyrin derivatives, poly(vinylcarbazole), poly(silylene), poly(thiophene), and other conductive polymers.

Examples of the light emitting compound other than the benzo[a]fluoranthene compound of the present invention include: fused ring aromatic compounds (including naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, and rubrene); quinacridone derivatives; acridone derivatives; coumarin derivatives; pyran derivatives; Nile red; pyrazine derivatives; benzoimidazole derivatives; benzothiazole derivatives; benzoxazole derivatives; stilbene derivatives; organometallic complexes (including organic aluminum complexes such as tris(8-quinolinolato)aluminum, and organic beryllium complexes); and high-molecular derivatives such as poly(phenylene vinylene) derivatives, poly(fluorene) derivatives, poly(phenylene) derivatives, poly(thienylene vinylene) derivatives, and poly(acetylene) derivatives.

Examples of the electron transportable compound include oxadiazole derivatives, oxazole derivatives, triazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and organometallic complexes.

A desirable anode material has as large a work function as possible. Examples of available anode include: metal elements such as gold, platinum, silver, copper, nickel, palladium, cobalt, selenium, vanadium, and tungsten, and alloys thereof; and metal oxides such as tin oxide, zinc oxide, indium oxide, indium tin oxide (ITO), and indium zinc oxide. Further, conductive polymers such as polyaniline, polypyrrole, polythiophene, and polyphenylene sulfide may also be used. Each of those electrode substances may be used singly. Alternatively, two or more of them may also be used in combination. Further, the anode may be formed of a single layer and may be formed of multiple layers.

A desirable cathode material has as small a work function as possible. Examples of available cathode include: metal elements such as lithium, sodium, potassium, calcium, magnesium, aluminum, indium, ruthenium, titanium, manganese, yttrium, silver, lead, tin, and chromium. Alternatively, those metal elements may be used in combination as alloys. For example, the following alloys can be used: lithium-indium, sodium-potassium, magnesium-silver, aluminum-lithium, aluminum-magnesium, and magnesium-indium alloys. Further, metal oxides such as indium tin oxide (ITO) may also be used. Each of those electrode substances may be used singly or in combination of two or more. Further, the cathode may be formed of a single layer and may be formed of multiple layers.

Substrates which may be used in the present invention include: opaque substrates such as metallic substrates and ceramics substrates; and transparent substrates such as glass, quartz, and plastic sheet substrates, but are not particularly limited to these materials.

In addition, a color filter film, a fluorescent color converting film, a dielectric reflection film, or the like may be used in the substrate to control emitted light. The device of the present invention can also be produced by being connected to a thin-film transistor (TFT) produced on a substrate.

Moreover, with respect to a direction of extracting light of the device, both a bottom emission structure (structure in which light is extracted from the substrate side) and a top emission structure (structure in which light is extracted from a side opposite to the substrate) can be acceptable.

The organic light emitting device of the present invention is produced by a method such as a vacuum vapor deposition method, a solution application method, a transfer method involving the use of laser or the like, or a spray method. Here, an organic layer containing the benzo[a]fluoranthene compound of the present invention is preferably formed by, for example, the vacuum vapor deposition method or the solution application method because the crystallization or the like of the layer itself to be formed hardly occurs, and the layer is excellent in stability over time.

Hereinafter, the present invention will be further specifically described with reference to Examples, but is not limited thereto.

EXAMPLE 1

Synthesis of Exemplified Compound A-1

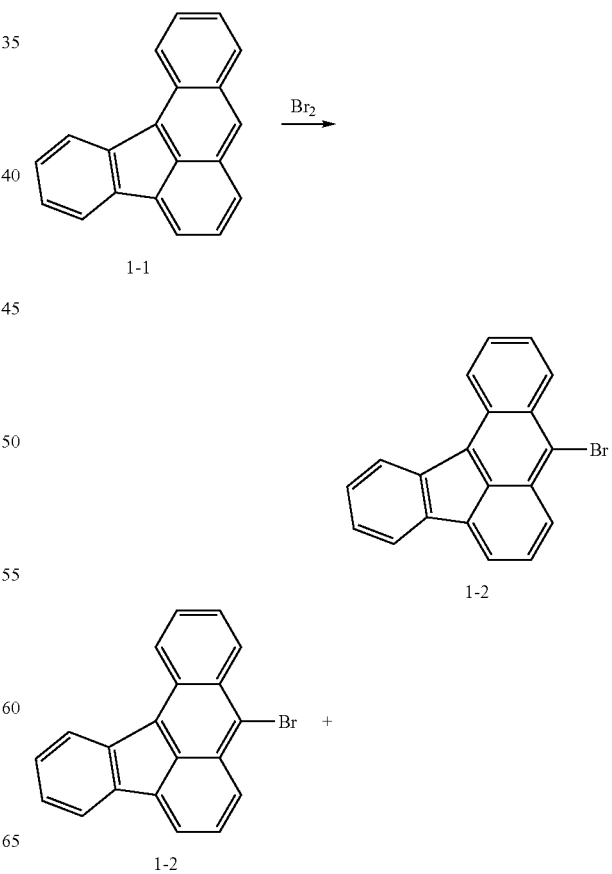

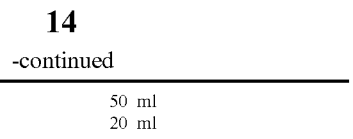

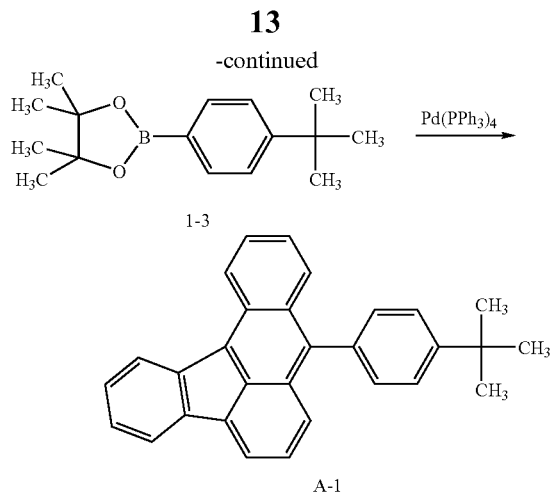

(a) Synthesis of Intermediate Compound 1-2

A reagent and a solvent shown below were loaded into a 200-ml three-necked flask.

Compound 1-1: 1.0 g (3.96 mmol)
Dichloromethane: 50 ml

Next, a solution prepared by mixing 0.20 ml of bromine and 10 ml of dichloromethane was dropped to the mixture while the mixture was stirred under a nitrogen atmosphere and under ice cooling. Next, the reaction solution was stirred for 5 hours. After the completion of the reaction, the reaction solution was filtrated, and the resultant crystal was washed with methanol, whereby 1.24 g of Intermediate 1-2 as a yellow crystal were obtained (95% yield).

(b) Synthesis of Exemplified Compound A-1

Reagents and solvents shown below were loaded into a 200-ml three-necked flask.

| Compound 1-2: | 0.500 g (1.51 mmol) |
|---|---|
| Compound 1-3: | 0.432 g (1.66 mmol) |
| Toluene: | 50 ml |
| Ethanol: | 20 ml |

Next, an aqueous solution prepared by mixing 1.35 g of cesium carbonate and 50 ml of water was dropped to the reaction solution while the reaction solution was stirred under a nitrogen atmosphere at room temperature. Subsequently, 0.174 g of tetrakis(triphenylphosphine)palladium(0) was added to the reaction solution. Next, the temperature of the reaction solution was increased to 77° C., and the reaction solution was stirred for 5 hours. After the completion of the reaction, the organic layer was extracted with toluene and dried with anhydrous sodium sulfate, and then the solvent was removed by distillation under reduced pressure. Next, the remainder was purified by silica gel column chromatography (developing solvent: a mixed solvent of toluene and heptane), whereby 0.476 g of Exemplified Compound A-1 as a yellow crystal was obtained (82% yield).

Mass spectrometry confirmed that Exemplified Compound A-1 had an M+ of 384.

In addition, $^1$H-NMR measurement identified the structure of Exemplified Compound A-1.

$^1$H-NMR (CDCl$_3$, 400 MHz) σ (ppm): 8.84 (d, 1H), 8.44 (d, 1H), 8.05-7.99 (m, 3H), 7.73 (d, 1H), 7.69-7.65 (m, 1H), 7.60 (d, 2H), 7.57 (dd, 1H), 7.50 (t, 1H), 7.45 (d, 2H), 7.44-7.40 (m, 2H), 1.48 (s, 9H)

In addition, an emission spectrum in a dilute solution of Exemplified Compound A-1 in toluene having a concentration of $10^{-6}$ mol/l was measured. As a result, the emission spectrum showed a good green color having an emission peak at 505 nm. It should be noted that the emission spectrum was measured with a fluorophotometer (F-4500 manufactured by Hitachi, Ltd.) at an excitation wavelength of 340 nm.

Each of Exemplified Compounds A-3, A-5, A-6, A-9, A-10, A-11, and A-12 can be synthesized by using the corresponding one of the pinacolborane derivatives shown in Table 1 below instead of Compound 1-3 in the section (b) of Example 1.

TABLE 1

| Exemplified Compound | Pinacolborane derivative |
|---|---|
| A-3 | ![structure] |
| A-5 | ![structure] |
| A-6 | ![structure] |

TABLE 1-continued

| Exemplified Compound | Pinacolborane derivative |
|---|---|
| A-9 | 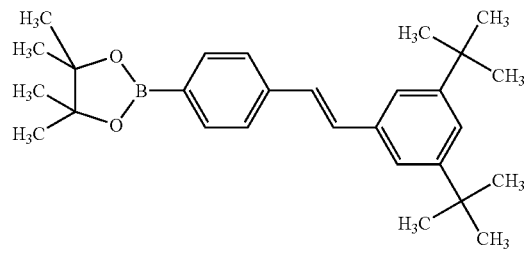 |
| A-10 | 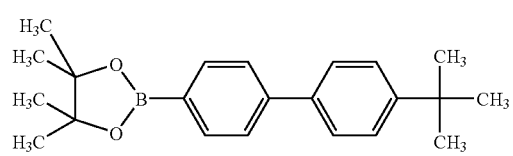 |
| A-11 | 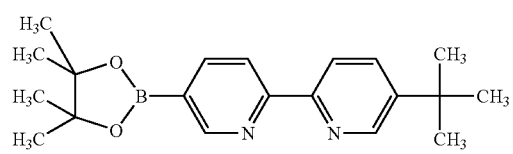 |
| A-12 | 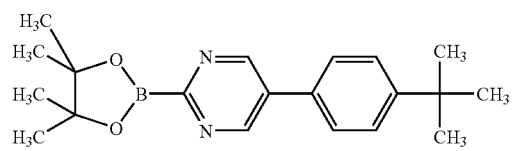 |

EXAMPLE 2

Production of Organic Light Emitting Device

As an anode, a film of tin oxide indium (ITO) having a film thicknesses of 120 nm was formed on a glass substrate by a sputtering method. Next, the obtained substrate thus formed was subjected to ultrasonic cleaning with acetone and isopropyl alcohol (IPA) subsequently. Then, the resultant was washed in boiling IPA, followed by drying. Further, the resultant was subjected to UV/ozone cleaning. The thus-treated glass substrate was used as a transparent conductive supporting substrate.

Next, a 0.1 wt % solution of Compound 2-1 shown below in chloroform was formed into a film having a thickness of 20 nm on the transparent conductive supporting substrate by a spin coating method, whereby a hole transporting layer was formed.

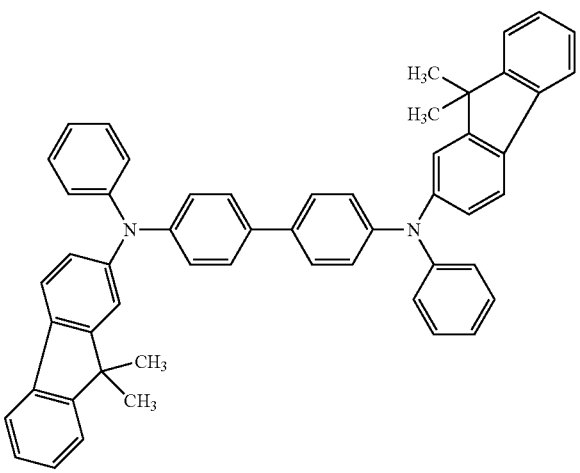

2-1

Next, any other organic layer and a layer of which a cathode was formed were continuously formed by a vacuum vapor deposition method based on resistance heating in a vacuum chamber at $10^{-5}$ Pa. To be specific, first, Exemplified Compound A-1 as a guest and Compound 2-2 shown below were co-deposited at a weight concentration ratio of 5:95 so as to serve as a light emitting layer. At that time, the thickness of the light emitting layer was 20 nm. Next, Compound 2-3 shown below was formed into an electron transporting layer having a thickness of 40 nm. Next, LiF was formed into a metal electrode layer 1 having a thickness of 0.5 nm. Next, Al was formed into a metal electrode layer 2 having a thickness of 150 nm. Here, the metal electrode layer 1 and the metal electrode layer 2 each function as a cathode.

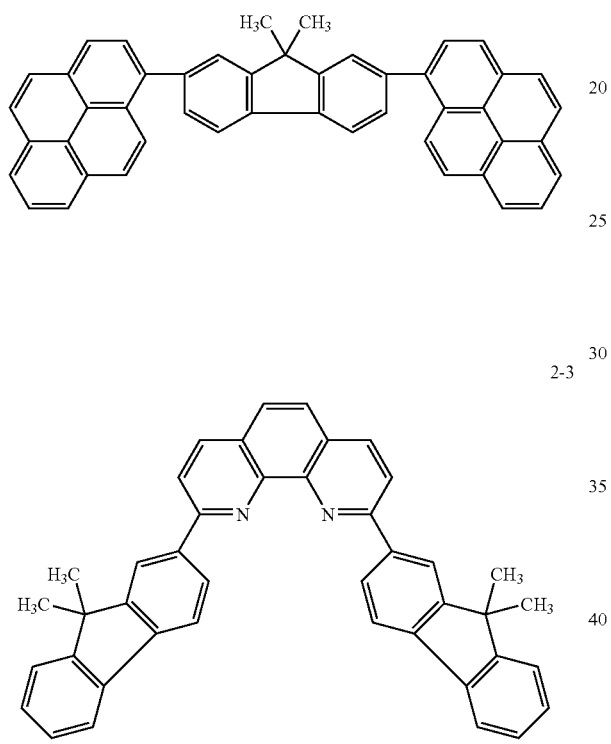

Thus, an organic light emitting device was produced.

A voltage of 6.1 V was applied to the organic light emitting device produced in this example. As a result, the device was observed to emit green light having an emission luminance of 1,560 cd/m² at a current density of 17 mA/cm².

Further, the organic light emitting device of this example was continuously driven for 100 hours under a nitrogen atmosphere while a current density was kept at 165 mA/cm². As a result, the percentage by which the luminance of the device degraded after the driving for 100 hours as compared to the initial luminance of the device was as small as 5% or less.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-130526, filed May 16, 2007, and Japanese Patent Application No. 2008-095675, filed Apr. 2, 2008, which are hereby incorporated by reference herein in their entirety.

The invention claimed is:

1. A benzo fluoranthene compound represented by the following general formula (I):

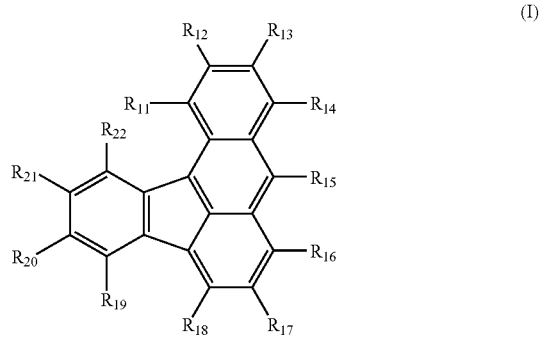

wherein $R_{20}$ is represented by a hydrogen atom, a substituted or unsubstituted alkyl group, or $R_m$; $R_{15}$ represents $R_m$; and $R_m$ is represented by the following general formula (i):

wherein $Ar_1$ represents a substituted or unsubstituted phenylene group;

wherein $X_1$ represents an isopropyl group, a t-butyl group or an adamantyl group; and wherein each of $R_{11}$ to $R_{14}$, $R_{16}$ to $R_{19}$, $R_{21}$, and $R_{22}$, independently, is represented by $R_m$ or is selected from the group consisting of a hydrogen atom, a halogen atom, a cyano group, a nitro group, a substituted or unsubstituted alkyl group, a substituted or unsubstituted alkoxy group, a substituted or unsubstituted alkenyl group, a substituted or unsubstituted alkynyl group, a substituted or unsubstituted aralkyl group, and a substituted or unsubstituted amino group.

2. The benzo fluoranthene compound according to claim 1, wherein $R_{20}$ is a hydrogen atom or a substituted or unsubstituted alkyl group.

3. An organic light emitting device comprising:

an anode;

a cathode; and one or more layers each containing an organic compound, the one or more layers being interposed between the anode and the cathode, wherein at least one layer of the one or more layers each containing an organic compound contains at least one kind of the benzo[a]fluoranthene compound according to claim 1.

4. The organic light emitting device according to claim 3, wherein the benzo[a]fluoranthene compound is contained in a light emitting layer.

5. The organic light emitting device according to claim 4, wherein the light emitting layer comprises the benzo[a]fluoranthene compound as a guest and a compound represented by the following formula

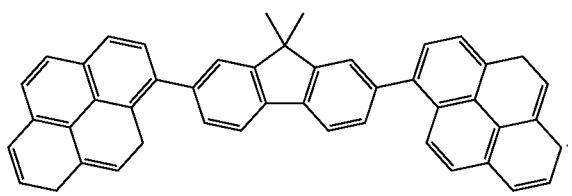
6. The organic light emitting device according to claim 3, further comprising a color filter.
7. An apparatus comprising a substrate and the organic light emitting device according to claim 3.
8. A display apparatus comprising the organic light emitting device according to claim 3 and a transistor.
* * * * *